US008889111B2

(12) United States Patent
Wood et al.

(10) Patent No.: US 8,889,111 B2
(45) Date of Patent: *Nov. 18, 2014

(54) COMPOSITION FOR THE PERMANENT SHAPING OF HUMAN HAIR

(75) Inventors: Jonathan Wood, Weinheim (DE); Bernd Nöcker, Ober-Ramstadt (DE); Sandra Schmelz, Marktheidenfeld (DE); Britta Punsch, Kesselsdorf (DE); Jörg Schneider, Griesheim (DE)

(73) Assignee: KAO Germany GmbH, Darmstadt (DE)

(*) Notice: Subject to any disclaimer, the term of this patent is extended or adjusted under 35 U.S.C. 154(b) by 315 days.

This patent is subject to a terminal disclaimer.

(21) Appl. No.: 12/939,383

(22) Filed: Nov. 4, 2010

(65) Prior Publication Data

US 2011/0044926 A1 Feb. 24, 2011

Related U.S. Application Data

(62) Division of application No. 11/567,305, filed on Dec. 6, 2006, now Pat. No. 7,850,953.

(30) Foreign Application Priority Data

Dec. 16, 2005 (EP) .................................... 05027635

(51) Int. Cl.
  *A61Q 5/04* (2006.01)
  *A61K 8/18* (2006.01)
  *A61K 8/35* (2006.01)

(52) U.S. Cl.
  CPC .. *A61K 8/355* (2013.01); *A61Q 5/04* (2013.01)
  USPC .......................................... 424/70.2; 424/70.1

(58) Field of Classification Search
  None
  See application file for complete search history.

(56) References Cited

U.S. PATENT DOCUMENTS

| 3,935,868 | A | * | 2/1976 | Zeffren et al. ................. 132/209 |
| 4,366,827 | A | * | 1/1983 | Madrange et al. ............ 132/204 |
| 4,529,586 | A | | 7/1985 | De Marco et al. |
| 4,547,365 | A | | 10/1985 | Kubo et al. |
| 4,673,568 | A | | 6/1987 | Grollier et al. |
| 5,208,014 | A | | 5/1993 | Dubief et al. |
| 5,293,885 | A | | 3/1994 | Darkwa et al. |
| 5,332,570 | A | | 7/1994 | Bergstrom et al. |
| 5,441,729 | A | | 8/1995 | Salce et al. |
| 5,520,909 | A | | 5/1996 | Salce et al. |
| 5,565,192 | A | | 10/1996 | Leroy et al. |
| 5,972,993 | A | * | 10/1999 | Ptchelintsev ................. 514/449 |
| 6,080,788 | A | | 6/2000 | Sole et al. |
| 6,136,859 | A | | 10/2000 | Henriksen |
| 6,180,662 | B1 | | 1/2001 | Lanzendörfer et al. |
| 6,290,942 | B1 | | 9/2001 | Nakazato et al. |
| 6,376,455 | B1 | | 4/2002 | Friedli et al. |
| 6,378,530 | B1 | | 4/2002 | Rezvani et al. |
| 6,692,731 | B2 | | 2/2004 | Rose et al. |
| 6,855,312 | B1 | | 2/2005 | Craig et al. |
| 7,169,385 | B2 | | 1/2007 | Fantuzzi et al. |
| 7,850,953 | B2 | | 12/2010 | Wood et al. |
| 2001/0008631 | A1 | | 7/2001 | Ellis et al. |
| 2001/0028887 | A1 | | 10/2001 | Douin et al. |
| 2004/0146476 | A1 | * | 7/2004 | Shami ........................ 424/70.14 |
| 2004/0237218 | A1 | | 12/2004 | Marsh et al. |
| 2007/0020214 | A1 | | 1/2007 | Muller et al. |
| 2007/0141005 | A1 | * | 6/2007 | Wood et al. .................. 424/70.2 |
| 2008/0279803 | A1 | | 11/2008 | Kainz et al. |

FOREIGN PATENT DOCUMENTS

| DE | 19926177 A1 | 12/2001 |
| DE | 10360688 A1 | 7/2005 |
| EP | 0712623 A | 5/1996 |
| EP | 1059081 | 12/2000 |
| EP | 1391194 | 2/2004 |
| EP | 1598047 | 11/2005 |
| EP | 1797861 A | 6/2007 |
| GB | 2157168 A | 10/1985 |
| WO | 8907435 A2 | 8/1989 |
| WO | 2005115315 A1 | 12/2005 |
| WO | 2006056361 A | 6/2006 |

OTHER PUBLICATIONS

Koller et al, EP1059081 Machine Translation, 2000, pp. 1-5.*
Dow Corning 949 Cationic Emulsion; INCI Name: Amodimethicone and cetrimonium chloride and trideceth-12; pp. 1-3.
Product Information; Information About Dow Corning 2-8194 Microemulsion(1998).
Principles of Polymer Science and Technology in Cosmetics and Personal Care; edited by E. Desmond Goddard, et al., p. 299 (1999).
Dow Corning(R) 2-8177 Emulsion; Dow Corning Corporation; Material Safety Data Sheet; pp. 1-8; Version 1.3 (2009).
CAS Registry No. RN 68131-40-8, Copyright 2010 ACS on STN.
Isomer: Structural Isomers-Infoplease.com: Structural Isomers; http://www.infoplease.com/ce6/sci/A0858924.html. pp. 1 and 2 (2007).

* cited by examiner

*Primary Examiner* — Blessing M Fubara
*Assistant Examiner* — Jennifer A Berrios
(74) *Attorney, Agent, or Firm* — Norris McLaughlin & Marcus PA

(57) ABSTRACT

The present invention concerns a composition for the permanent shaping of human hair used both for the permanent waving of human hair with an excellent waving effect as well as for the straightening of curled hair comprising at least one ubichinone of the formula

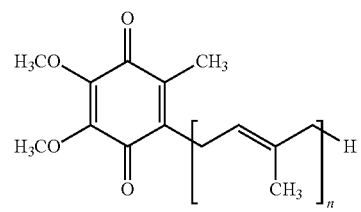

where n is a number between 1 and 10 at a concentration of 0.0001 to 1% by weight calculated to total composition.

12 Claims, No Drawings

COMPOSITION FOR THE PERMANENT SHAPING OF HUMAN HAIR

This application is a divisional of U.S. Ser. No. 11/567,305, which was filed on Dec. 6, 2006, now U.S. Pat. No. 7,850,953, which claims foreign priority benefit under 35 U.S.C. §119 of the European Patent Application No. 05 027 635.1 filed Dec. 16, 2005.

The present invention concerns a composition for the permanent shaping of human hair used both for the permanent waving of human hair with an excellent waving effect as well as for the straightening of curled hair.

It is generally known that permanent waving is carried out in two steps, the reductive splitting of the cysteine disulfide bonds in the hair by a reducing agent, and the subsequent neutralization by application of an oxidizing agent, whereby the cysteine disulfide bonds are restored.

The reducing agent still most frequently used today is thioglycolic acid, also in form of the salts thereof, in particular its ammonium salt, although numerous other thio compounds have been proposed for this purpose, which, however, mostly did not succeed.

The compositions containing thioglycollates are customarily applied at a pH-value between 7 and 10, in particular 8.5 and 9.5.

Such compositions vary in their waving and/or straightening performance and, therefore, there is still need for further improvement.

The present invention starts from the task of providing a composition for the permanent shaping of human hair with excellent waving and straightening performance. Hair waved or straightened with composition disclosed herein looks and feels natural upon touching by hand.

Accordingly, the first object of the present invention is a composition for permanent shaping and/or straightening hair based on at least one reducing agent, which further comprises at least one ubichinone of the formula

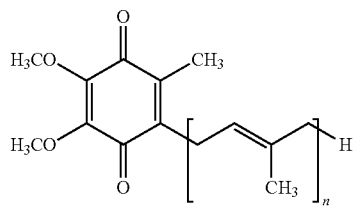

where n is a number between 1 and 10. Preferred ubichinones are the ones where n is a number between 6 and 10 and especially preferred is Ubichinone 50 where n is 10, also known as Coenzyme Q10.

Ubichinones have been used in cosmetic compositions. Such compositions have been disclosed for example in EP 751 762 B1 for hair conditioning compositions in combination with retinols, in DE 199 26 167 A1 and DE 199 26 168 A1 for hair styling compositions, DE 199 26 170 A1 for cleansing preparations and in DE 199 26 156 A1 for hair conditioning compositions. Furthermore, in EP 1232 741 A1 the use of ubichinones in hair coloring compositions is disclosed.

In none of the patent documents mentioned above, a permanent shaping composition for hair comprising ubichinone is neither disclosed nor mentioned.

Concentration of at least one ubichinone of the above formula in permanent shaping compositions of the present invention is from 0.0001 to 1%, preferably from 0.0002 to 0.75%, more preferably from 0.0002 to 0.5% and most preferably from 0.0005 to 0.5% by weight, calculated to total composition.

The permanent waving compositions according to the invention comprises at least one reducing compound. Preferred are thioglycolic acid and thiolactic acid as well as the salts thereof, in particular the ammonium and ethanolamine salts. Further useful thio compounds are in particular cysteine or the hydrochloride thereof, homocysteine, cysteamine, N-acetyl cysteine, thioglycerol, ethanediol monothioglycollate, 1.2-propyleneglycol monothioglycollate (see also WO-A 93/1791), 1-3-propanediol monothioglycollate or the isomer mixture resulting therefrom, 1.3-butanediol and 1.4-butanediol monothioglycollate and the isomer mixtures therefrom, polyethylene glycol, such as di-, tri- and tetraethyleneglycol monothioglycollates, glycerol monothiolactate and further thio acids and the esters thereof, as well as mixtures thereof.

The use of inorganic reducing sulfur compounds such as sodium hydrogen sulfite is basically also possible.

The total reduction agent content in the compositions according to the invention customarily amounts from 2.5% to about 15% by weight, calculated to total composition as free thioglycolic acid as reference substance.

The waving compositions containing reducing agents can, if necessary, comprise alkalizing agents. Their quantity is dependent on the reducing agent and the desired pH-value of the composition. Reducing agent compositions preferably contain about 0.1% to about 5%, in particular about 0.5% to about 2.5% by weight thereof, calculated to the total composition. Alkalizing agents preferred within the scope of the invention are ammonium carbamate, ammonia and/or ammonium(bi)carbonate, and triethanolamine. It is desirable to adjust the pH-value between about 6.5 and 10.5, preferably about 7 to 9.5.

The shaping compositions according to the invention are suited for use both for the permanent waving, i.e. curling of human hair and for the straightening, i.e. smoothing thereof.

The viscosity best suited for the permanent waving compositions according to the invention proved to be in the range of about 500 to 10,000 mPa·s, preferably about 1,000 to about 5,000 mPa·s, measured at 20° C. in a Brookfield viscosimeter (no. 5 spindle), whereas the viscosity suited for the straightening compositions is preferably higher in a range up to about 50,000 mPa·s, preferably up to 30,000 mPa·s measured at 20° C. in a Brookfield viscosimeter (no. 5 spindle).

The viscosity is adjusted by addition of the appropriate amounts of thickening agents known per se, such as cellulose derivatives. Thickening may as well be realized by formulating a composition in form of an emulsion with the use of $C_{10}$-$C_{22}$-fatty alcohols, in admixture with long mono alkyl chain quaternary ammonium surfactants.

The permanent waving compositions according to the present invention preferably comprise surfactants selected from anionic, nonionic, cationic and amphoteric ones. Their proportion ranges from about 0.05% to about 10%, in particular from about 0.1% to about 5% by weight, calculated to total composition.

Suitable anionic surfactants are especially the known alkyl ether sulfates and carboxylic acids, in particular in form of their alkali salts, as well as protein fatty acid condensates.

Suitable nonionic surfactants, which are preferred within the scope of the invention, are in particular $C_8$-$C_{18}$-fatty alcohol polyglycol ethers, fatty acid polyglycol esters, fatty acid alkanolamides, aminoxides, and especially $C_8$-$C_{18}$-alkyl polyglucosides.

Also possible is the incorporation of amphoteric surfactants, such as the known alkyl betaines, alkyl amido betaines, and alkyl amphoacetates.

Further according to a further preferred embodiment, permanent shaping compositions comprise at least one cationic surfactant according to general formula

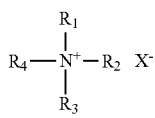

where $R_1$ s a saturated or unsaturated, branched or non-branched alkyl chain with 8-22 C atoms or

where $R_5$ is saturated or unsaturated, branched or non-branched alkyl chain with 7-21 C atoms and n has typical value of 0-4 or

where $R_6$ is saturated or unsaturated, branched or non-branched alkyl chain with 7-21 C atoms and n has typical value of 0-4, and $R_2$ is a hydrogen, saturated or unsaturated, branched or non-branched alkyl chain with 1-22 C atoms or

where $R_5$ is saturated or unsaturated, branched or non-branched alkyl chain with 7-21 C atoms and n has typical value of 0-4 or

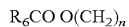

where $R_6$ is saturated or unsaturated, branched or non-branched alkyl chain with 7-21 C atoms and n has typical value of 0-4, and $R_3$ and $R_4$ are independent from each other H or lower alkyl chain with 1 to 4 carbon atoms, and X is chloride, bromide or methosulfate.

Concentration of at least one cationic surfactant is in the range from 0.05% to 5%, preferably 0.1% to 2.5% by weight, calculated to total composition.

Suitable long-chain quaternary ammonium compounds which can be used alone or in admixture are in particular cetyl trimethyl ammonium chloride, dimethyl dicetyl ammonium chloride, trimethyl cetyl ammonium bromide chloride, stearyl trimethyl ammonium chloride, dimethyl stearyl benzyl ammonium chloride, benzyl tetradecyl dimethyl ammonium chloride, dimethyl dihydrogenated tallow ammonium chloride, lauryl pyridinium chloride, lauryl dimethyl benzyl ammonium chloride, lauryl trimethyl ammonium chloride, tris-(oligooxyethyl) alkyl ammonium phosphate, cetyl pyridinium chloride, etc.

In a further preferred embodiment of the present invention, the compositions comprise at least one cationic polymer. Basically suitable are all cationic polymers listed under the generic name "Polyquaternium" and "Quaternium" in the CTFA International Cosmetic Ingredient Dictionary. Examples are Polyquaternium 6, Polyquaternium 7, Polyquaternium 10, Polyquaternium 11, Polyquaternium 16, Polyquaternium 22 and Polyquaternium 28, Polyquaternium 39, Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

The cationic polymers also include the quaternized products of graft polymers from organopolysiloxanes and polyethyl oxazolines described in EP-A 524 612 and EP-A 640 643.

Concentration of one or more cationic polymers is in the range from 0.05% to 5%, preferably 0.1% to 2.5% by weight, calculated to total composition.

Permanent shaping compositions of present invention can comprise additionally at least one organic solvent. Suitable organic solvents are 2-methyl-1,3-propanediol, mono and dialcohols or the ethers thereof, in particular mono-$C_1$-$C_3$-alkyl ether, ethanol, n-propanol, isopropyl alcohol, 1-methoxypropanol, 1-ethoxypropanol and ethoxydiglycol, diols and their esters 1,3- and 1,4-butanediol, diethyleneglycol and the monomethyl and monoethyl ether thereof, dipropylene glycol and the monomethyl and monoethyl ether thereof, glycerol, hexanetriol, ethyl carbitol, benzyl alcohol, benzyloxy ethanol, propylene carbonate, N-alkyl pyrrolidone, and urea or their mixture preferably in an amount from about 0.1% to 10% by weight, calculated to the total composition.

Permanent shaping composition of the present invention can comprise further ceramide type of compound with the general formula

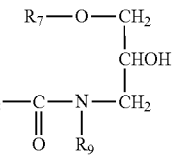

where $R_7$ and $R_8$ are independent from each other alkyl- or. alkenyl group with 10 to 22 carbon atoms, $R_9$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide.

Further optional ingredient are sterols, especially the phytosterols as preferred hair restructuring agents. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

Optionally fatty acids of C10 to C22 may be incorporated into the compositions of the present invention at a concentration of preferably 0.01 to 2.5% by weight calculated to total composition.

Another preferred compound in the permanent shaping composition of the present invention is silicone compounds and especially aminated silicones such as amodimethicone available from for example Dow Corning under the brand names Dow Corning 949 Emulsion and Dow Corning 2-8194. Concentration of silicones, especially amodimethicone, is in the range of 0.05 to 2.5%, preferably 0.1 to 1% by weight calculated to total composition.

Additionally, one or more natural oil component may be incorporated into the compositions of the present invention. Suitable are such as olive oil, almond oil, avocado oil, wheatgerm oil, ricinus oil or their mixture. Concentration of these natural oil ingredients should be 0.01 to 2.5%, preferably 0.01. to 1%, more preferably 0.05 to 0.5% by weight, calculated to total composition.

The compositions used according to the invention can naturally comprise all the substances customarily found in permanent shaping compositions, a list of which will not be given here, and are preferably present as solutions, gels with a higher or lower viscosity, emulsions or creams. They can be single-phase products or compositions packed into separate packaging which are united upon application, as they are disclosed, for example, in DE-C 43 04 828.

In order to avoid repetition, reference is here made to the state of the art as it is described, for example, in "Ullmann's Encyclopedia of Industrial Chemistry", Vol. A12 (1986), pages 588 to 591, and in particular to the monography of K. Schrader, "Grundlagen und Rezepturen der Kosmetika", $2^{nd}$. Ed. (1989, Hüthig Buchverlag) pages 823 to 840, as well as the article by D. Hollenberg et. al. in "Seifen-Öle-Fette-Wachse", 117 (1991), pages 81 to 87.

Composition of the present invention is used in a process for permanent waving wherein hair is washed or shampooed first and wound on the curlers, subsequently a reducing agent comprising composition with at least one ubichinone is applied onto hair and after 1 to 45 min, preferably 1 to 30 min of processing time, depending on the hair strength, rinsed off from hair with tap water and an oxidizing composition comprising at least one oxidizing agent, preferably hydrogen peroxide or sodium bromate at a concentration of 0.5 to 10% by weight calculated to total of oxidizing composition, is applied onto hair and left on the hair 1 to 20 min and rinsed off and curlers removed from hair. In cases where additional conditioning composition is required this may as well be applied.

In another process as described above the curlers are removed after rinsing off the reducing agent and before applying the oxidizing agent.

Further in another process, after rinsing off the reducing agent from hair, an intermediate treatment composition is applied onto hair and without rinsing off but after removing the excess amount of intermediate treatment with a towel, oxidizing composition is applied and at the end of the processing they are rinsed off from hair and curlers are removed from hair. It has further been found out that the use of ubichinone in the intermediate treatment composition in the same concentration range as disclosed above for the reducing composition improves the permanent shaping of hair as well in terms of curl appearance and natural look and feel of hair. Therefore in another preferred form of the present invention, permanent shaping of hair is carried our with a process wherein hair is washed or shampooed first and subsequently a reducing agent comprising composition is applied onto hair and after 1 to 45 min, preferably 1 to 30 min of processing time, depending on the hair strength, rinsed off from hair with tap water and an intermediate treatment composition comprising at least one ubichinone of the formula above and magnesium sulfate at a concentration of 2 to 15% by weight is applied and without rinsing off an oxidizing composition comprising at least one oxidizing agent, preferably hydrogen peroxide or sodium bromate at a concentration of 0.5 to 10% by weight calculated to total of oxidizing composition, is applied onto hair and left on the hair 1 to 20 min and rinsed off. In cases where additional conditioning composition is required this may as well be applied.

The intermediate treatment composition has a pH value between 2.5 to 6, preferably 3 to 5.5 and most preferably 3 to 5.

A straightening process may also be carried out in a different process wherein hair is washed and/or shampooed and dried and reducing composition comprising at least one ubichinone is applied onto dry hair and processed for 5 to 60 min, preferably 5 to 45 min and rinsed off with water and dried and the dry hair physically straighten with hot iron at a temperature of 130 to 210° C. and subsequently an oxidizing composition comprising at least one oxidizing agent, preferably hydrogen peroxide or sodium bromate at a concentration of 0.5 to 10% by weight calculated to total of oxidizing composition, is applied onto hair and left on the hair 1 to 20 min and rinsed off.

The following examples are to illustrate the invention, but not to limit it.

EXAMPLE 1

Alkaline Permanent Wave for Normal Hair

| | |
|---|---|
| Ammonium thioglycolate (60%) | 21.3 (% by wt. |
| Ammonium hydrogen carbonate | 5.0 |
| 1,3-butylene gylcol | 3.0 |
| Amodimethicone | 0.2 |
| PEG-40-Hydrogenated castor oil | 0.7 |
| Polyquaternium-7 | 0.5 |
| Perfume | 0.4 |
| Coenzyme Q10 | 0.04 |
| Ammonia, 25% | ad pH 8.3 |
| Water | ad 100.0 |

With this composition the hair was permanently waved for about 15 minutes, rinsed and neutralized for about 8 minutes with a customary 2.5% $H_2O_2$ composition. Homogeneous wave appearance was obtained. Exclusion of Coenzyme Q10 resulted in less homogeneous perm appearance.

EXAMPLE 2

Alkaline Permanent Wave for Damaged Hair

| | |
|---|---|
| Ammonium thioglycollate (60%) | 15.0 (% by wt.) |
| Ammonium hydrogen carbonate | 2.5 |
| Ceteth-20 | 0.7 |
| Tallow trimonium chloride | 0.1 |
| 1,3-butylene gylcol | 0.5 |
| Polyquaternium-6 | 1.5 |
| Amodimethicone | 0.2 |
| Coenzyme Q10 | 0.1 |
| Oleic acid | 0.05 |
| Perfume | 0.4 |
| Ammonia, 25% | ad pH 8.0 |
| Water | ad 100.0 |

The permanent wave achieved with this composition was similar to the one obtained with the composition according to Example 1.

Exclusion of the ubichinone led to waves with substantially weaker contours.

EXAMPLE 3

Alkaline Permanent Wave for Damaged Hair

| | |
|---|---|
| Ammonium thioglycollate (60%) | 0.9 (% by wt.) |
| Cystein hydrochloride | 5.7 |
| Ammonium hydrogen carbonate | 1.5 |

-continued

| | |
|---|---|
| Acetylcystein | 0.7 |
| Cetrimonium chloride | 0.1 |
| 1,3-butylene gylcol | 0.5 |
| Polyquaternium-39 | 1.5 |
| Amodimethicone | 0.2 |
| Coenzyme Q10 | 0.1 |
| Oleic acid | 0.05 |
| Perfume | 0.4 |
| Ammonia, 25% | ad pH 9.8 |
| Water | ad 100.0 |

The permanent wave achieved with this composition was similar to the one obtained with the composition according to Example 1.

Exclusion of the ubichinone led to substantially weaker waves.

EXAMPLE 4

Neutral Permanent Wave for Normal Hair

A permanent waving product consisting of two Compositions A and B, filled into a two-chamber packaging the chambers of which were kept separate until application, was prepared by destruction of the separating wall and applied onto human hair rolled onto curlers. The hair was rinsed after about fifteen minutes processing and neutralized for about five minutes with a 2.5% $H_2O_2$ neutralizer composition, rinsed again, shampooed and dried.

An expressive, even, intensive permanent wave was obtained.

An identical treatment which had no Ubichinone showed a visibly inferior wave.

Composition A:

| | |
|---|---|
| Ammonium hydrogen carbonate | 4.5 (g) |
| Polyquaternium-6 | 1.0 |
| PEG-65-Hydrogenated castor oil | 0.8 |
| Isopropyl alcohol | 1.5 |
| Ethoxydiglycol | 2.0 |
| Cocoamidopropyl betaine | 1.0 |
| Perfume | 0.3 |
| Coenzyme Q10 | 0.05 |
| Turbidifying agent | 0.5 |
| Ammonia, 25% | ad pH 8.4 |
| Water | ad 72.0 |

Composition B:

| | |
|---|---|
| Ammonium thioglycollate, 70% | 18.0 (g) |
| Thiolactic acid | 2.0 |
| 2-Methyl-1.3-propanediol | 0.5 |
| Ammonia, 25% | ad pH 5.5 |
| Water | ad 28.0 |

After admixture of both Compositions a ready-to-use product with a pH-value of 7.4 was obtained.

EXAMPLE 5

Neutral Permanent Wave for Dyed Hair

A permanent waving product filled into a two-chamber package was prepared in analogy to Example 3:

Composition A:

| | |
|---|---|
| Ammonium hydrogen carbonate | 3.5 (g) |
| Polyquaternium-11 | 0.5 |
| Ethanol | 0.5 |
| 1-Methoxypropanol | 1.0 |
| Cocoamidopropyl betaine | 1.0 |
| PEG-25-glyceryl cocoate | 0.8 |
| Coenzyme Q10 | 0.1 |
| Oleic acid | 0.05 |
| Perfume | 0.3 |
| Turbidifying agent | 0.5 |
| Ammonia, 25% | ad pH 8.3 |
| Water | ad 72.0 |

Composition B:

| | |
|---|---|
| Ammonium thioglycollate, 70% | 13.0 (g) |
| Thiolactic acid | 0.5 |
| 2-Methyl-1.3-propanediol | 1.5 |
| Ammonia, 25% | ad pH 5.5 |
| Water | ad 28.0 |

A product with a pH-value of 7.4 was obtained by admixture of the Compositions immediately prior to application. After application onto dyed hair as described in Example 3, this mixture resulted in an expressive permanent wave, which had not effect whatever on the color gloss and color intensity.

EXAMPLE 6

Alkaline Permanent Waving Gel

| | |
|---|---|
| Ammonium thioglycollate, 70% | 15.0 (g) |
| Ammonium hydrogen carbonate | 4.5 |
| PEG-40-Hydrogenated castor oil | 0.7 |
| $C_{12}$-$C_{18}$-Fatty alcohol mixture | 3.5 |
| Cetrimonium chloride | 2.0 |
| Amodimethicone | 0.05 |
| 2-Methyl-1.3-propanediol | 0.5 |
| Polyquaternium-28 | 0.1 |
| Coenzyme Q10 | 0.1 |
| Perfume | 0.3 |
| Ammonia, 25% | ad pH 8.0 |
| Water | ad 100.0 |

Intermediate Treatment Composition

| | |
|---|---|
| Asparagic acid | 0.25% by weight |
| Glutamic acid | 0.50 |
| Alanin DL | 0.25 |
| Magnesium sulfate | 10.00 |
| Coenzyme Q10 | 0.05 |
| Water | q.s. to 100 |

The above composition had a pH of 4.10.

EXAMPLE 7

Straightening Composition

| | |
|---|---|
| Thioglycolic acid | 8.0 (% by wt.) |
| $C_{16}$-$C_{22}$-Fatty alcohol mixture | 3.5 |
| Oleth-50 | 2.5 |
| Laureth-23 | 1.5 |
| Polyquaternium-2 | 0.8 |
| Coenzyme Q10 | 0.1 |
| Oleic acid | 0.1 |
| Ethanol | 5.0 |
| Perfume | 0.6 |
| Monoethanolamine | ad pH 9.3 |
| Water | ad 100.0 |

This composition constitutes an effecting smoothing composition for kinky hair.

The invention claimed is:

1. A process for permanent waving of hair comprising the steps of:
   (i) washing or shampooing hair;
   (ii) winding the washed or shampooed hair on curlers;
   (iii) applying to the hair a first composition comprising at least one reducing agent selected from the group consisting of thioglycolic acid, thiolactic acid, and salts of thiolactic acid, and at least one ubiquinone according to the formula

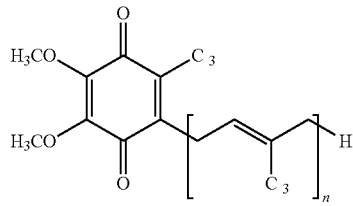

where n is a number between 1 and 10, wherein the reducing agent is present in the formulation at a concentration between 5 to 15 wt. %, calculated to the total composition;
   (iv) processing the composition on the hair for between 1 to 45 minutes;
   (v) rinsing the first composition from the hair;
   (vi) applying to the hair a second composition comprising between about 0.5 to 10 wt. % of at least one oxidizing agent;
   (vi) processing the second composition on the hair for between about 1 to 20 minutes; and
   (vii) rinsing the second composition from the hair.

2. The process according to claim 1 wherein the ubiquinone is present in the first composition at a concentration of between about 0.0001 to 1.0 wt. %, calculated to the total composition.

3. The process according to claim 1 wherein the first composition has a Brookfield viscosity of between 500 to 10,000 mPa·s at 20° C.

4. The process according to claim 1 wherein the first composition comprises at least one surfactant selected from anionic, nonionic, cationic and amphoteric surfactants, and is present at a concentration of 0.05 to 10% by weight, calculated to the total composition.

5. The process according to claim 1 wherein the first composition comprises at least one cationic polymer at a concentration of 0.05 to 5% by weight, calculated to the total composition.

6. The process according to claim 1 wherein the first composition further comprises at least one organic solvent at a concentration of 0.1 to 10% by weight, calculated to the total composition.

7. The process according to claim 1 wherein the first composition comprises at least one silicone compound at a concentration of 0.05 to 2.5% by weight, calculated to the total composition.

8. The process according to claim 1 wherein the first composition comprises at least one fatty acid with 10 to 22 C atoms at a concentration of 0.01 to 2.5% by weight, calculated to the total composition.

9. The process according to claim 1 wherein the oxidizing agent in the second composition is hydrogen peroxide or sodium bromate.

10. The process according to claim 1 wherein the reducing agent is present in the first composition at a concentration of between about 5 to 8 wt. %, calculated to the total composition.

11. A process for straightening hair comprising the steps of:
   (i) washing or shampooing hair;
   (ii) applying to the hair a first composition comprising at least one reducing agent selected from the group consisting of thioglycolic acid, thiolactic acid, and salts of thiolactic acid, and at least one ubiquinone according to the formula

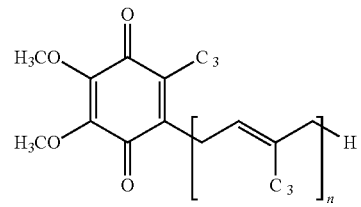

where n is a number between 1 and 10, wherein the reducing agent is present at a concentration between 5 to 15 wt. %, calculated to the total composition
   (iii) processing the composition on the hair for between 5 to 60 minutes;
   (iv) rinsing the first composition from the hair;
   (v) drying the hair;
   (vi) physically straightening the hair with a means for straightening hair
   (vii) applying to the hair a second composition comprising between 0.5 to 10 wt. % of at least one oxidizing agent;
   (viii) processing the second composition on the hair for between 1 to 20 minutes; and
   (ix) rinsing the second composition from the hair.

12. The process according to claim 11 wherein the means for straightening hair is a hot iron.

* * * * *